United States Patent [19]

Razaq et al.

[11] Patent Number: 5,164,053
[45] Date of Patent: Nov. 17, 1992

[54] ELECTROCHEMICAL GAS SENSOR AND METHOD OF USING SAME

[75] Inventors: Mohammad Razaq, Hacienda Heights; Atulbhai S. Shah, San Dimas; Harold W. Pust, Huntington Beach, all of Calif.

[73] Assignee: Teledyne Industries, Inc., Los Angeles, Calif.

[21] Appl. No.: 513,091

[22] Filed: Apr. 23, 1990

[51] Int. Cl.$^5$ .................... G01N 27/26; G01N 27/407
[52] U.S. Cl. .............................. 204/153.18; 204/421; 204/424; 204/431; 204/432
[58] Field of Search ................ 204/421, 153.1, 153.18, 204/424, 431, 432; 429/33

[56] References Cited

U.S. PATENT DOCUMENTS

| | | | |
|---|---|---|---|
| 2,913,511 | 11/1959 | Grubb | 429/30 |
| 3,316,161 | 4/1967 | Jung et al. | 429/12 |
| 3,342,558 | 9/1967 | Reinecke | 429/12 |
| 3,767,552 | 10/1974 | Lauer | 204/195 |
| 3,776,832 | 12/1974 | Oswin et al. | 204/195 R |
| 4,025,412 | 5/1977 | LaConti | 204/432 |
| 4,044,193 | 8/1977 | Petrow et al. | 429/40 |
| 4,077,861 | 3/1978 | Lauer | 204/195 P |
| 4,647,359 | 3/1987 | Lindstrom | 204/294 |
| 4,718,991 | 1/1988 | Yamazoe et al. | 204/421 X |
| 4,795,533 | 1/1989 | Young et al. | 204/421 X |
| 4,820,386 | 4/1989 | LaConti et al. | 204/153.18 X |
| 4,828,941 | 5/1989 | Sterzel | 429/33 |
| 5,085,760 | 2/1992 | Razaq et al. | 204/431 |

FOREIGN PATENT DOCUMENTS 6610435 1/1968 Netherlands .......... 429/33

OTHER PUBLICATIONS

"The Oxide Handbook" edited by G. V. Samsonov 1973, pp. 266-274.
"Instrument Engineers Handbook", 2nd Edition, Section 11.21, pp. 825-826.
"Elements of Materials Science and Engineering", L. H. Van Vlack, 4th Edition, p. 302.
A. J. Polak et al., Sensors and Actuators, 9, pp. 1-7, (1986).
R. P. Hamlen et al., "Immobilized Phosphoric Acid Intermediate-Temperature Fuel Cell".
"Electrochemical Technology", vol. 4 (No. 3-4), pp. 172-174, Mar.-Apr. 1966.
R. P. Hamlen, "Ionic Conductivity of Zirconium Phosphate", Journal of Electrochemical Society, vol. 4 (No. 3-4) pp. 746-749 Aug. 1966.
"Fuel Cells", a Review of Government Sponsored Research, 1950-1964 NASA SP 1210, pp. 26 and 27.
"Nafion Resins", E. I. duPont Technical Information Bulletin No. AL-163 (undated prior art).
"Development of Small Polymer Fuel Cell", Watkins et al. Proceedings of 32nd Power Series Conference, Cherry Hill, N.J. Jun. 9-12, 1986, The Electrochemical Society, pp. 590-595.
"The Strem Chemiker" Apr., 1984, vol. X, No. 1, 3 pages.

Primary Examiner—T. Tung
Attorney, Agent, or Firm—Edward J. DaRin

[57] ABSTRACT

An electrochemical gas sensor having a solid ionic conductive electrolyte therein and adapted to sense trace levels of reactive gases in the parts per million range. The electrochemical sensing cell has a pair of catalytic electrodes attached to the opposite sides of the solid electrolyte. The sensing cell is supported and contained to permit the distribution of reactant gases over the electrode surfaces for reacting thereat and thereby providing an external electrical current flow representative of the quantity of the reactant gas undergoing sensing.

7 Claims, 2 Drawing Sheets

ELECTROCHEMICAL GAS SENSOR AND METHOD OF USING SAME

FIELD OF INVENTION

This invention relates to electrochemical gas sensors for electrically signalling the concentration of an electrochemically active gas, such as hydrogen and oxygen, in a gas mixture and, more particularly, to a sensing cell utilizing a solid electrolyte capable of sensing electrochemically active gases in ranges down to parts per million.

CROSS-REFERENCE

This invention is an electrochemical gas sensor of the type disclosed in the earlier filed copending application bearing Ser. No. 404,680 and assigned to the same assignee as the present invention, in that the invention disclosed herein is also an electrochemical gas sensor capable of sensing reactive gases in the parts per million (p.p.m.) range. The aforementioned application was abandoned and refiled as a continuation application bearing Ser. No. 563,811 on Aug. 6, 1990 and issued as U.S. Pat. No. 5,085,760 on Feb. 4, 1991. The present invention, however, utilizes a solid electrolyte element, rather than an aqueous electrolyte solution, as is typical of known, prior art electrochemical gas sensors and the gas sensor disclosed in the aforementioned copending patent application utilizes an aqueous electrolyte solution.

BACKGROUND OF INVENTION

One of the major problems associated with the present day, known electrochemical gas sensors that utilize an aqueous electrolyte solution is the loss of water from the sensor during the sensing operations. When these prior art sensors are utilized and if the gases to be sensed are not humidified prior to applying them to the electrochemical gas sensor, the loss of water from the sensor may even be severe. The loss of water from these prior art electrochemical gas sensors can significantly affect the output signal as well as the life of the sensor. Certain types of electrochemical gas sensors can be used continuously by adding water to the sensor's body periodically, typically once a month. Some gas analyzers, such as the Teledyne Analytical Instruments Model 306WA Trace Oxygen Analyzer, have the capability to humidify the gas prior to exposure of gas to the electrochemical sensor. To utilize such equipment, however, adds substantial complications to an analysis procedure and particularly in the control of the extent to which the gases are humidified. As should be apparent, the improper control of the gas humidification of the gases undergoing sensing could either increase or decrease the water level in the sensor and, accordingly, adversely affect the output signals derived from the sensor. At the present time, therefore, there is no other known solution to the loss of water problem from an aqueous electrolyte solution.

Solid, ionic conductive elements are known and have been used in hydrogen-oxygen fuel cells, as is well-known to those skilled in the fuel cell art. The use of such solid, ionic conductive electrolyte elements in an electrochemical gas sensor, however, has not been heretofore proposed or used in such electrochemical gas sensors to solve the problems of the loss of water in the typical prior art gas sensor, as we presently understand the prior art.

SUMMARY OF INVENTION

The present invention provides an improved, inexpensive and significantly simpler construction for an electrochemical gas sensor as well as a simplified operation without the prior problems of the drying of the electrolyte used in the sensor. The electrochemical gas sensing cell of the present invention is capable of sensing concentrations of electrochemically active gases in gas mixtures in the parts per million range, as well. The use of a solid electrolyte element in the gas sensor eliminates the problem of the loss of water in sensors utilizing the aqueous electrolyte solution. The present invention utilizes a solid ionic polymer membrane that when equilibrated with water, causes the membrane to achieve significant ionic conductivity at room temperatures and, when properly treated, up to temperatures of 180 degrees Centigrade. The polymer membrane is utilized with a high surface area, metal catalyzed gas diffusion electrodes for both the anode and cathode electrodes. The anode may have a platinum catalyzed metal, while the oxygen sensing cathode electrode may have a platinum, or silver, or gold catalyzed element. The cathode electrode, then, will sense the quantity of oxygen in the gas mixture applied thereto while hydrogen will be fed to the anode electrode in proportion to the general requirements of the quantity of the oxygen that is contained in the gas mixture applied to the cathode. The same cell may be utilized for sensing hydrogen in the gas mixture with the amount of oxygen applied to the cell being of a known concentration.

The method comprehended by the present invention is one for sensing the concentration of electrochemically reactive gas in a gas mixture, including concentrations in the parts per million range, as well as the steps of providing a solid electrolyte membrane capable of being rendered ionic conductive when equilibrated with water or phosphoric acid. The method includes a pair of catalytic electrode means at opposite sides of the solid membrane with each electrode means being attached to an individual side of the solid membrane, each of the electrodes being constructed of a high surface area metal catalyzed gas diffusing electrode. The method then comprehends distributing a gas mixture having a reactive gas therein to one of the electrodes for causing an electrochemical reduction of the active gas thereat and producing water, while distributing another gas of known concentration to the other electrode means to cause an electrochemical oxidation thereof for producing an electronic charge that flows between the electrodes during the electrochemical reactions.

From a specific structural standpoint, the electrochemical sensing cell comprises a solid ionic conductive electrolyte element with anode catalytic electrode means and cathode catalytic electrode means arranged at opposite sides of the solid element and attached to the solid element whereby in combination they constitute the sensing cell. The anode and cathode electrode means are characterized as a composite structure with electrically conducting gas diffusion hydrophobic surfaces and having the electrically conductive hydrophobic gas diffusing layer adapted for conveying gas therethrough and a catalyst layer of a high surface area metal dispersed on the high surface area carbon support. Container means enclose the sensing cell, including means for supporting the thus defined electrochemical sensing cell whereby the anode and cathode electrode surfaces are exposed within the container. The sensing cell includes means for continuously circulating a gas mixture having an unknown quantity of an electrochemcially active gas therein to be sensed for exposure to the gas diffusion surface of one of the electrode means to be diffused therethrough to the catalyst layer to be reacted thereat and means for circulating a gas of a known constant concentration for exposure to the gas diffusing surface of the other electrode means to be diffused therethrough to the catalyst layer. The gases applied to the electrodes are selected for producing the reactions at the electrodes to cause the thus generated electronic charge to flow between the electrodes through an external circuit for signalling the sensed concentration of the reactive gas in the applied gas mixture.

BRIEF DESCRIPTION OF THE DRAWINGS

These and other features of the present invention may be more fully appreciated when considered in light of the following specification and drawings, in which.

DETAILED DESCRIPTION OF THE PREFERRED EMBODIMENT

Figure 1:
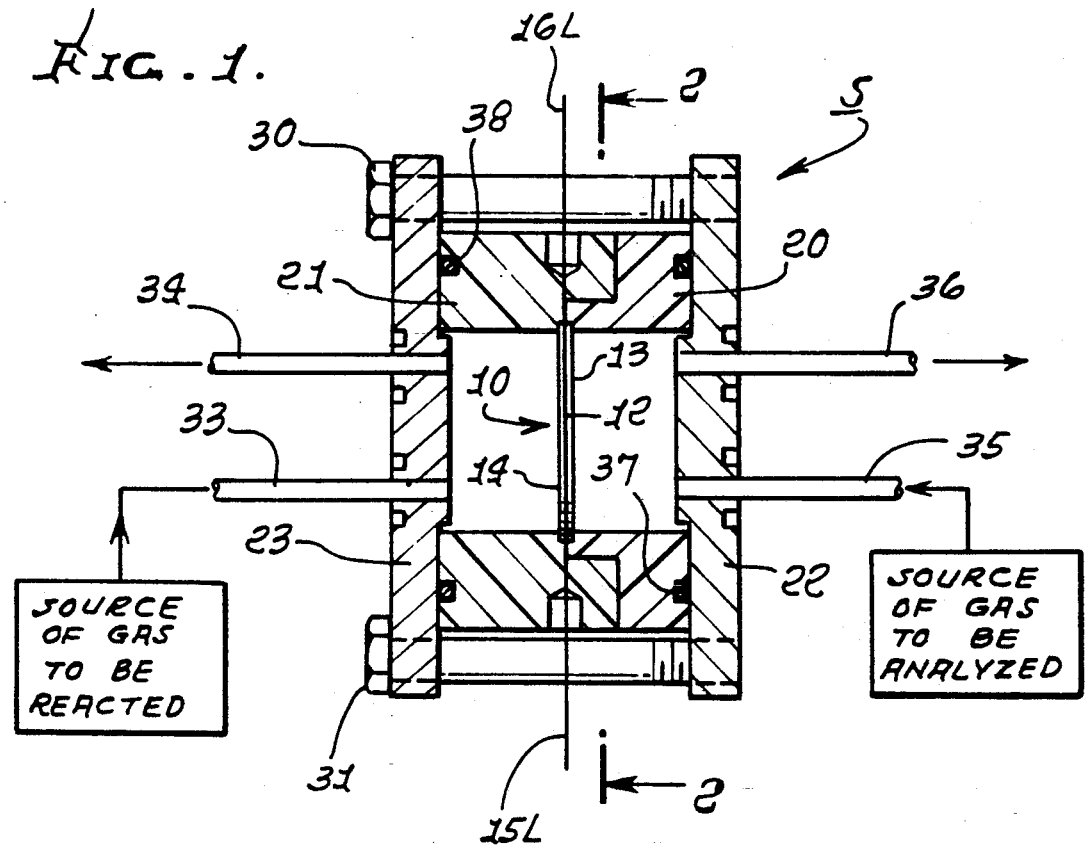
FIG. 1 is a cross-sectional front view of an electrochemical gas sensor, illustrating the sources of gases diagrammatically and embodying the present invention.

The present invention contemplates solving the problem of electrochemical gas sensors utilizing an aqueous electrolyte solution associated with the loss of water from the sensor during its use, by the use of a solid ionic conductive electrolyte, preferably in the form of a solid, ionic polymer as the electrolyte element. In addition, the electrochemical gas sensor having a solid electrolyte is contemplated for use in sensing gas traces in the parts per million (ppm) range. An example of a solid ionic polymer element that may be used in an electrochemical gas sensor of the type under consideration is commercially available from the E. I. duPont de Nemours & Company, Inc., of Wilmington, Del. Similar ionic conductive polymers are available from the Dow Chemical Company of Midland, Mich. Prior to embarking on the detailed disclosure of the electrochemical gas sensor utilizing an ionic conductive, solid element as the electrolyte, it would facilitate the understanding of the present invention if the functioning of the solid electrolyte material is in mind. A solid ionic conductive polymer that is manufactured and sold by the duPont Company under the trademark "NAFION" will be described. The polymer strand of the duPont ionic polymer consists of perfluorinated carbon chains with ether linkage and a sulfonic acid group attached at the end of the polymer strand as is represented by the following general structure:

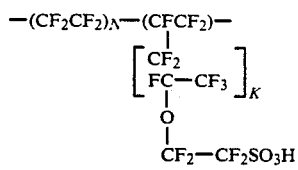

The equivalent weight of the aforementioned duPont solid ionic polymer is 1100 and the molecular weight is more than a million. Reference may be made to the duPont Technical Information Bulletin, Number AL-163, on "Nafion Resins" for a more detailed description of this product and which disclosure is incorporated herein by reference.

It is known that when the duPont solid ionic polymer is equilibrated with water, the sulfonic groups protonate water molecules, and, as a result, the solid polymer membrane achieves significant ionic conductivity at room temperature. The loss of the protonated water from said duPont solid ionic polymer is insignificant at room temperature and is therefore in itself a solution to the loss of water in the prior art type of electrochemical sensors. However, it has been found that at temperatures greater than 50 degrees Centigrade, the water from the selected solid ionic polymer will be slowly lost, and, as a result, the ionic conductivity of the element will accordingly decrease. This will render the polymer resin unsuitable for use as a solid electrolyte in an electrochemical cell at these higher temperatures.

It has been found that the ionic conductivity of the polymer element can be maintained even at temperatures above room temperature, up to 180 degrees Centigrade, provided the polymer membrane is pre-equilibrated with phosphoric acid by soaking the membrane in phosphoric acid at 100 degrees Centigrade for several hours. At 100 degrees Centigrade water from the Nafion element is lost and to the most extent is replaced by phosphoric acid (98 percent) since the sulfonic groups of the Nafion element can easily protonate the phosphoric acid molecules. At the 180 degree Centigrade temperature, phosphoric acid contains less than 4 percent by weight water. This will then permit the ionic conductivity of the polymer element to be maintained at temperatures up to 180 degrees Centigrade. Since the vapor pressure of phosphoric acid at 180 degrees Centigrade is relatively low, the loss of phosphoric acid from the membrane will be insignificant at the 180 degrees temperature and ionic conductivity of the polymer membrane will not be seriously affected at this higher temperature. At temperatures greater than 180 degrees Centigrade the Nafion element slowly degrades and adversely affects the kinetics of the electrochemical reactions at the electrode surfaces, and therefore the sensor shows unstable output over extended periods of time, i.e., the sensor becomes useless. The protonated form of the solid polymer carries the ionic charge from one electrode to another of a sensing cell during the electrochemical reactions at the anode and cathode electrodes provided for the cell. The use of a solid ionic polymer as a solid electrolyte element in hydrogen-oxygen fuel cells is well-known to those working in the fuel cell art. As is indicated hereinabove, the use of a solid polymer electrolyte pre-equilibrated with phosphoric acid in an electrochemical gas sensor, however, has not been reported to date, and no such disclosure is known to the applicants herein. It has been found that the use of a solid polymer electrolyte in an electrochemical gas sensor of the type under consideration would significantly simplify the sensor design and the operation thereof and avoid the problems of the prior art type of gas sensor utilizing the aqueous electrolyte solutions and the loss of water therefrom. With the use of a such a pre-equilibrated solid electrolyte element there would be no free electrolyte in the resulting sensor and, therefore, there would be no danger from the sensor becoming dry during its operation and thereby inoperative, or impaired in operation.

Figure 3:
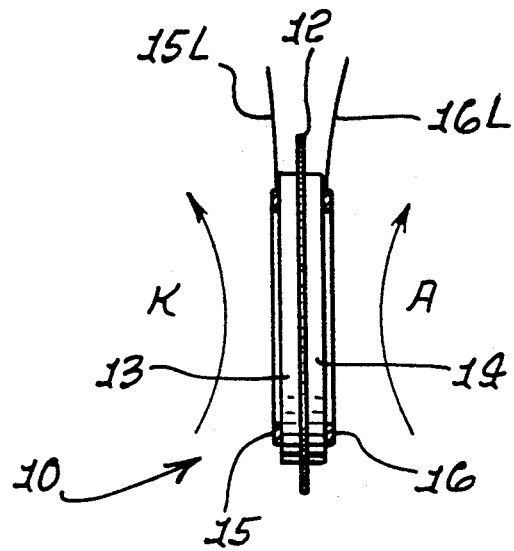
FIG. 3 is an enlarged diagrammatic illustration of the assembled components of the cell outside of the sensor of FIG. 1.

Now referring to the drawings and specifically to FIG. 3, the configuration of the cell 10 utilized in the sensor of the present invention will be first examined in detail based on a schematic representation of the cell 10 therein. The solid electrolyte selected for use in the cell 10 and illustrated in FIG. 3 as the element 12 is constructed of the resin identified as a "Nafion" resin of E. I. duPont de Nemours Company, Inc., as discussed hereinabove. The important characteristic of the solid electrolyte element 12 is that the "Nafion" resin is a perfluorinated ion-exchange polymer that becomes ionic conductive when equilibrated with water or other molecules which are protonated by the sulfonic group of the "Nafion" element. The solid electrolyte membrane 12 selected for use in the cell 10 of the present invention has a circular configuration of 1.25 inches in diameter and a thickness of 7/1000 of an inch (7 mils). The cell 10 is completed by sandwiching the membrane 12 between two high surface area metal catalyzed gas diffusion electrodes 13 and 14, respectively, identifying the cathode and anode electrodes of the cell 10. The cathode electrode 13 and anode electrode 14 are constructed identically, and each has a diameter of 0.92 inches and a thickness of 17/1000 of an inch. The cathode electrode 13 has a silver, Ag, catalyst thereon while the anode electrode 14 has a platinum, Pt, catalyst thereon. The electrodes that may be utilized in accordance with the present invention are commercially available from Prototech Company of Newton, Mass., and other suppliers. Specifically, the structural organization of such electrodes is well-known for use in fuel cells and is disclosed in detail in U.S. Pat. No. 4,647,359 and assigned to said Prototech Company. The commercial embodiments of such electrodes as disclosed in the Prototech patent are available from the Prototech Company and are useful in the sensor S. The presently preferred embodiment of the electrode that is commercially available is identified as a gas diffusion electrode on Toray paper and has been utilized in the sensor S. The disclosure of U.S. Pat. No. 4,647,359 is incorporated herein by reference. Although such electrodes are utilized in fuel cells for generating electric power, there is no known utilization of such electrodes in electrochemical gas analyzers of the type which is the subject of the present invention and, particularly, in sensing gas traces, such as oxygen and hydrogen in the parts per million range. The use of high surface area metal catalyzed gas diffusion electrodes affords the possibility of achieving much higher effective surface areas for the electrodes of an electrochemical gas analyzing cell without increasing its geometric area. The typical effective surface area of a gas diffusion electrode may be up to 600 times greater than its geometric area when compared to a smooth, metal screen electrode where the effective area is usually twice the geometric area. The aforementioned commercially available electrodes useful in the present invention typically may have a high surface area for the catalyst surface of at least 150 $m^2$/gram, (150 square meters per gram). In terms of particle sizes of metal catalyst, the sizes fall within the 15-25 Angstroms range. The relationship of particle sizes and surface area is well-known in the prior art, and this particle size relates to a surface area of 178-112 $m^2$/gram.

The electrodes 13 and 14 are a composite structure having a gas diffusing Teflon-carbon backing layer on one side thereof bonded to a relatively thin layer of high surface area catalyst metal dispersed on a high surface area carbon support. The gas diffusing portions of the electrodes consist of a microporous structure of Teflon and carbon mixture. The microporous structure functions as gas wicks to convey the gas subjected thereto through the microporous, electrically conductive, hydrophobic structure of the Teflon-carbon mixture to the catalyst surface. This gas receiving and diffusing layer permits the conveyance of the gas therethrough by means of the gas wicks formed by Teflon-carbon structures. The catalyst layer of the cathode is a relatively thin layer having approximately 1/10th of the thickness of the backing layer. This layer can be termed the catalyst layer as it is exposed to the solid electrolyte of the cell S. The catalyst layer consists of a high surface area metal catalyst, such as silver, platinum, gold and the like metals, dispersed on a high surface area carbon support. A relatively small amount of Teflon or a plymeric, fluorinated hydrocarbon material is used as a binder of the metallic catalyst to the carbon support. The electrodes 13 and 14 may e utilized without a backing layer and still be operative and those types of electrodes are also commercially available from the above identified Prototech Company. The thus defined gas diffusing layers of the electrodes 13 and 14 allow the gases to be analyzed to diffuse through its micorporous structure and reach the metallic catlyst surfaces where an electrochemically active gas, such as oxygen, reacts.

As illustrated in FIG. 3, a metal ring 15 is secured to the cathode electrode 13 in electrical contact with the electrode and provided with a lead wire 15L connected to the ring 15 for use as an output lead terminal. Similarly, the anode electrode 14 has a metal ring 16 secured adjacent the ends thereof with its individual output lead 16L connected to the ring 16. The cell 10 functions, for example, when a gas mixture having an unknown concentration of oxygen is delivered to the cathode electrode 13 and a reactive gas such as hydrogen is coupled to the anode electrode 14. Assuming these operating conditions, the cell 10 will have the overall reactions at the anode electrode 14 and the cathode electrode 13 as follows:

$$H_2 \longrightarrow 2H^+ + 2e \qquad \text{anode - 14}$$

$$O_2 + 4H^+ + 4e \longrightarrow H_2O \qquad \text{cathode - 13}$$

During the reaction at the cathode electrode 13, the anode electrode 14 will give off hydrogen ions and electrons. The electrons thus released at the anode electrode flow to the cathode electrode through an external circuit with a magnitude proportional to the oxygen concentration of the gas applied to the cathode. As the aforementioned equations symbolize during the operation of the cell 10, water is produced at the cathode electrode 13. The amount of water produced at the cathode electrode 13 will depend on the concentration of oxygen in the gas mixture applied to the electrode and the length of time for which the sensor S is used. Since the gases to be sensed are usually dry, water concentration will not build up in the sensors at least when the sensor S is used for sensing electrochemical, reactive gases with low oxygen concentrations for relatively short periods of time. If the sensor is to be used for sensing gases with high concentrations of oxygen for longer periods of time, it would be advantageous to use the sensor S at temperatures above 50 degrees Centigrade to minimize the water buildup in the sensor S, as will be detailed hereinafter.

Now considering the treatment required of the "Nafion" resin membrane 12 for use at temperatures above room temperatures up to 180 degrees Centigrade, it will be noted that the resin membrane as received from the supplier is in the form of a sheet having a thickness of 7/1000 (7 mils) and is then cut into a circular configuration of a desired diameter (1.25 inches). Then it is normally cleaned using a dilute hydrogen peroxide and deionized water in accordance with the procedures well-known to those skilled in the art of handling such solid electrolyte materials. After the cleaning process, the membrane 12 is soaked in a concentrated phosphoric acid at a temperature of 100 degrees Centigrade for several hours, preferably for at least twelve hours. During this soaking period, most of the water in the membrane is replaced with the phosphoric acid. The membrane 12 is then removed from the phosphoric acid, wiped quickly and sandwiched between the electrodes 13 and 14 using a hydraulic press at approximately 1000 pounds per square inch. This assembly constitutes the electrochemical cell 10 and is then in condition to be housed for defining the sensor S.

Figure 2:
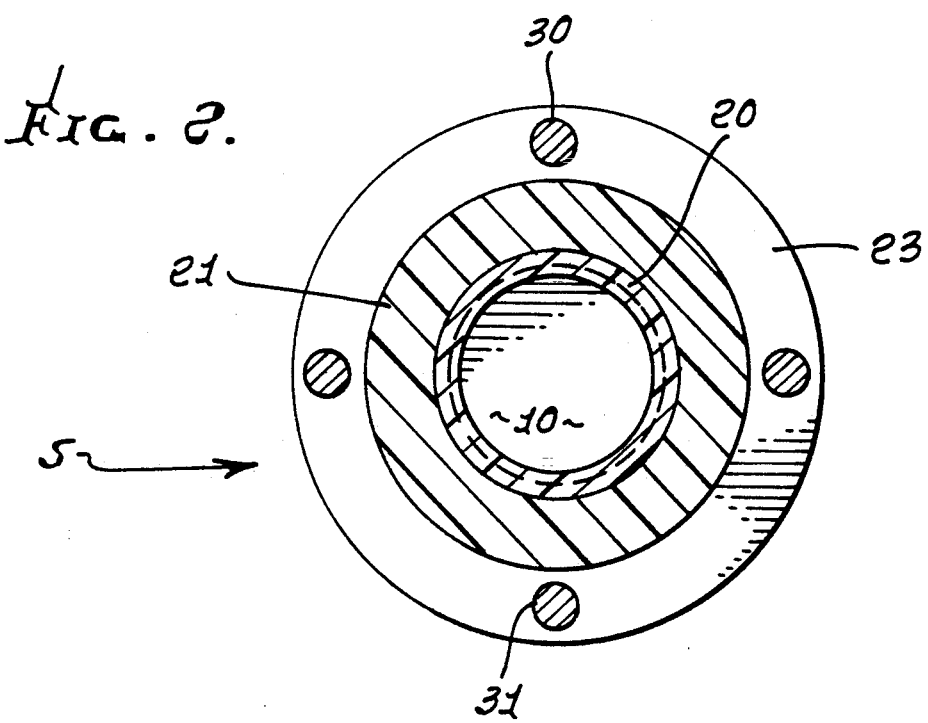
FIG. 2 is a view taken along the line 2—2 of FIG. 1.

With the construction of the cell 10 in mind and now referring to FIG. 1, the incorporation of the cell 10 in the sensor S as illustrated in FIGS. 1 and 2 will now be examined. The sensor 10 is first placed between two nonconductive blocks, such as a pair of acrylic plastic blocks 20 and 21 of a circular configuration. The blocks 20 and 21 each have an opening through their centers of an inside diameter of approximately 0.7 inches. The two blocks 20 and 21 with cell 10 placed centrally thereof, as illustrated, are secured together for holding the cell 10 in position by two stainless steel plates 22 and 23 arranged on opposite sides of the blocks 20 and 21, respectively. Each of the stainless steel plates 22 and 23 have stainless steel tubes welded thereto for circulating the gases to be sensed by the cell 10. The stainless steel plates 22 and 23 are secured together for securing the blocks 20 and 21 holding the cell 10 therebetween by means of the fasteners 30 and 31 secured in suitable apertures for each of the plates 22 and 23 adjacent the ends thereof with the heads of the fasteners 30 and 31 illustrated in FIG. 1 on the left hand side and threaded into suitable threaded apertures provided for the right hand plate 22.

Assuming that the cathode electrode 13 is illustrated on the right hand side of FIG. 1 and the anode electrode 14 on the left side, as illustrated, the cathode electrode 13 will have a silver catalyst secured thereto while the anode electrode 14 will have a platinum catalyst secured to the anode electrode. The system for delivering the gases to the anode and cathode electrodes in accordance with the above arrangement will include a tubular element 33 welded to the plate 23 for delivering the gas to the anode electrode 14 of the cell 10. The plate 23 is also provided with an outlet tubular element 34 spaced from the inlet tubular element 33 for causing the gas entering the tubular element 33 to be circulated past the high surface area platinum catalyzed anode electrode 14 and then exit through the tubular element 34. It will be recognized that when the hydrogen gas is coupled to the tubular element 33, the hydrogen will be oxidized at the anode electrode in accordance with the above described reaction equation giving off hydrogen ions and electrons. Similarly arranged with the cathode electrode 13 on the opposite side of the cell 10, there are provided two tubular elements 35 and 36 arranged in a spaced apart relationship and welded to the stainless steel plate 22. The tubular element 35 may function as an entry element for the gas containing the reactive gas to be sensed, such as oxygen, and coupled past the cathode electrode 13 and then exits the space between the electrode and the inside wall of the plate 22 by means of the exit tubular element 36, as indicated hereinabove. With the oxygen in the gas mixture applied to the cathode electrode, the oxygen would be reduced in accordance with the above identified equation. With the reactions taking place simultaneously at the anode and cathode electrodes, the current will flow between the electrodes and through the exterior circuit for sensing the oxygen concentration and providing an electrical output signal representative of the concentration of the sensed reactive gas or oxygen in the gas mixture coupled to the entry tubular element 35. FIG. 1 eliminates the conductive rings secured to the anode and cathode electrodes, illustrated in FIG. 3 merely for simplification purposes in view of the small sizes of the elements under consideration. The arrangement illustrated also includes sealing the blocks 20 and 21 by means of the O-rings 37 and 38 secured between the inner wall of the plate 22 and the block 20 and the inner wall of the plate 23 and the block 21, preventing the escape of the gases undergoing sensing coupled into the spaces on the opposite sides of the cell 10. The conductive lead wires 15L and 16L illustrated in FIG. 3 that are secured to their respective rings 15 and 16 are illustrated in FIG. 1 whereby the lead wire 15L functions as the cathode contact and is threaded through the blocks 20 and 21 at the bottom portions thereof, as is evident from FIG. 1 and the cathode contact lead is a wire constructed of metallic wire, while the lead wire 16L extends through the upper portions of the blocks 20 and 21 in the sealed relationship for providing the external output signal between the anode and cathode electrodes. The lead wire 16L is constructed of the same metallic wire as the lead wire 15L.

The sensor S utilizing the "Nafion" resin membrane 12 as the solid polymer electrolyte and a high surface area platinum catalyzed gas diffusion anode electrode 14 attached to the membrane 12 and a high surface area silver catalyzed gas diffusion cathode electrode 13 constructed as described hereinabove has been successfully operated. The sensor S response that resulted produced a linear output with varying concentrations. The output signal can be increased by wetting of the cathode or anode electrodes or by coating the electrode with a thin film of the "Nafion" resin by soaking the electrode in a "Nafion" resin solution. This, however, would require the gas diffusion electrode to be modified so as not to have the hydrophobic backing layer. Such gas diffusion electrodes are also available from the Prototech Company referenced hereinabove. The electrode, then, after being coated with a thin film of the selected resin, can be attached to the solid membrane 12 using pressure in a similar fashion as described hereinabove.

Figure 4:
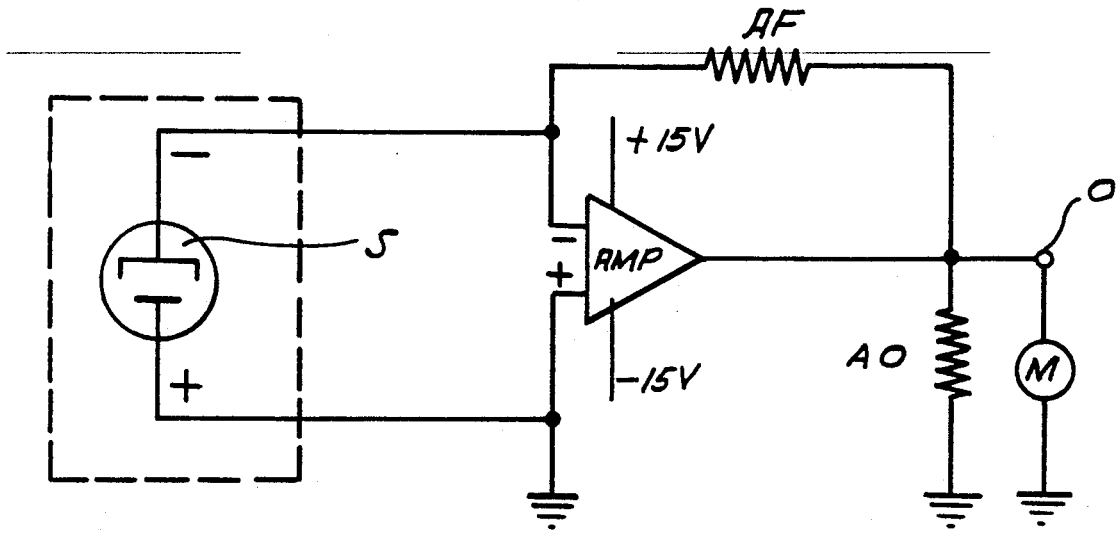
FIG. 4 is an electrical, schematic diagram of the sensing circuit for use with the electrochemical gas sensor of FIG. 1.

Now referring to FIG. 4, the electrical circuit for processing the electrical signals derived from the sensing cell S at suitable external cathode and the external anode terminals will be considered. Any conventional sensing circuit may be employed by coupling it to the external anode and cathode terminals and in FIG. 4, a conventional operational amplifier Amp is illustrated connected to the external anode and cathode terminals with the anode electrode illustrated connected to the negative input terminal of the amplifier Amp. The output circuit for the amplifier Amp is connected in series circuit relationship with an output resistor AO connected to a common voltage level or ground. A feedback resistor AF is connected between the output terminal common to the resistors AF and AO, to the negative input terminal of the amplifier Amp. A meter M may be connected between the output terminal O and ground that is calibrated to read the concentration of the sensed oxygen of the gas undergoing analysis for a direct read-out of the sensor S.

In the use of the sensor S, the concentrations of the electrochemically reactive gases such as hydrogen admitted to the anode electrode will be dependent on whether the gas to be analyzed has a high or low oxygen concentration. If the sensor S is to be used to analyze a gas which contains a low concentration of oxygen, in the parts per million (ppm) range or lower, the content of hydrogen gas in an inert gas such as nitrogen could be approximately 1 percent. If the quantity of oxygen to be sensed is at an approximately 1 percent level, pure hydrogen could be used at the anode electrode.

It should be noted that the same sensor S could be used as a hydrogen sensor with the same identical construction. This can be achieved by keeping the oxygen concentration that is coupled to the cathode electrode 13 constant while analyzing the gas mixture containing hydrogen at the anode electrode 14.

We claim:

1. An electrochemical sensing cell comprising a solid, perfluorinated, ion-exchange polymer electrolyte element with anode and cathode catalytic electrodes attached to the opposite sies of said solid polymer electrolyte, said polymer electrolyte element is further characterized as having been pre-equilibrated with an acid for maintaining teh ionic conductivity of said polymer electrolyte element at temperatures up to approximately 180 degrees Centigrade, one of the electrodes being characterized for causing the oxidation of a reactant gas distributed over the surface thereof with the other electrode causing the reduction of a reactant gas distributed over the surface thereof, means for containing and supporting the thus defined electrochemical sensing cell and for distributing reactant gases over the surfaces of teh anode and cathode electrode surfaces substantially simultaneously to thereby provide an electrical current representative of the quantity of the reactant gas undergoing sensing.

2. An electrochemical sensing cell comprising a solid, perfluorinated, ion-exchange polymer conductive element functioning as an electrolyte element, electrodes arranged on opposite sides of the solid conductive element with one surface of each element exposed for receiving gas distributed thereto and attached to said polymer element for constituting an electrochemical sensign cell, each of the electrodes being characterized as high surface area metal catalyzed gas diffusion electrodes for conveying gas therethrough when the exposed surfaces of the electrodes are subjected to preselected reactant gases for causing water to be produced at one electrode and hydrogen ions to be simultaneously produced at the other electrode upon the distribution of reactant gases over the electrode surfaces, said electrolyte element is further characterized as having been pre-equilibrated with an acid for maintaining the ionic conductivity thereof at temperatures up to approximately 180 degrees Centigrade, means for distributing a reactant gas of known concentration to one of the electrodes, and means for circulating a gas mixture having an unknown quantity of electrochemically reactive gas to the other electrode whereby said production of water and hydrogen ions occur substantially simultaneously at each electrode with the simultaneous application of the gas thereto for producing an electrical current flowing between the electrodes through an external circuit representative of the quantity of the sensed reactive gas on the gas mixture.

3. An electrochemical sensing cell for sensing the concentration of an electrochemically active gas in a gas mixture including concentrations in the parts per million range, comprising a solid, perfluorinated, ion-exchange polymer electrolyte element, an anode electrode and a cathode electrode arranged on opposite sides of said solid element and attached to the solid element thereby in combination constituting the electrochemical sensing cell, said eltrolyte element having been treated with an acid for pre-equilibrating said polymer for maintaining the ionic conductivity thereof at temperatures of up to approximately 180 degrees Centigrade, the anode and cathode electrodes are each constructed and defined as a composite structure with an electrically conducting high surface area support having a gas diffusing, hydrophobic surface on the side of the electrode opposite to the side attached to said solid element and having the electrically conducting, hydrophobic, gas diffusing surface adapted for conveying a gas therethrough and a catalyst surface of a high surface area metal dispersed on the high surface area electrically conductive surface, container means for enclosing the sensing cell including insulation means for supporting the thus defined electrochemical sensing cell whereby the anode and cathode electrode surfaces are exposed within the container means, and means for continuously circulating a gas mixture having an unknown quantity of electrochemically active gas therein to be sensed for exposure to the gas diffusion surface of one of said electrodes to be diffused therethrough to the catlyst layer to be reacted thereat, and means for continuously circulating a gas of a known, constant concentration for exposure to the gas diffusion surface of the other one of said electrodes to be diffused therethrough to the catalsyt lyaer, the gases applied to said electrodes being selected for producing reactions at the electrodes subjected to the mixture of the electrochemically active gas being sensed so that said active gas being sensed will react at the electrode it is exposed to so as to produce an amount of water dependent on the concentration of the active gas undergoing sensing with the other electrode being responsive to the gas of known concentration and reacting thereat to produce an electronic charge that flows between said electrodes during the electrochemical reactions for providing an electrical signal representative of the sensed concentration of the reactive gas in teh applied gas mixture whereby the sensor is maintained in operation up to approximately 180 degrees Centigrade without the need for water.

4. An electrochemical sensing cell as defined in claim 3 including circuit means adapted to be connected to said electrodes external of the sensing cell to be responsive to the electronic charge flowing between said electrodes for providing a sensing electrical signal related to the concentration of the sensed electrochemically active gas in the applied gas mixture.

5. An electrochemical sensing cell capable of sensign reactive gases in the parts per million range comprising a solid, perfluorinated, ion-exchange polymer electrolyte element, cathode and anode electrode elements attached to opposite sides of the solid element for defining the electrochemical sensing cell, said ionic conductive element is further characterized as having been pretreated with an acid for maintaining the ionic conductivity thereof at temperatures of up to approximately 180 degrees Centigrade, each electrode element being characterized as a high surface ara metal catalyzed gas diffusion electrode, the cathode element being a silver or gold catalyzed element with the anode element being a platinum catalyzed element, insulative means for enclosing the sensing cell whereby the cathode and anode elements are spaced from the side walls of the insulative means for permitting gases to be conveyed past the surfaces of the cathode and anode elements, individual electrically conducting elements secured to said elements and extending outside the insulative means for defining external elements for providing output signals traversing internally between the cathode and anode elements, means for circulating a gas mixture having oxygen therein to be conveyed past the cathode element, and means for conveying a gas mixture having hydrogen therein to be conveyed past the anode element.

6. An electrochemical sensing cell as defined in claim 5 wherein the solid polymer has been treated with phosphoric acid for maintaining the ionic conductivity of the polymer up to temperatures on the order of 180 degrees Centigrade.

7. A method for sensing the concentration of an electrochemically reactive gas in a gas mixture, including concentrations in the parts per million range, including the steps of providing a solid, perfluorinated, ion-exchange polymer electrolyte membrane that is ionic conductive and has been pre-treated with an acid to substantially eliminate any water in said membrane so there is no free liquid electrolyte present and thereby permitting the ionic conductivity of said membrane to be maintained at high temperatures up to approximately 180 degrees Centigrade, arranging a pair of electrodes on opposite sides of said solid membrane with each electrode being attached to an individual side of said membrane, each of the electrodes being a high surface area metal catalyzed gas diffusing electrode, applying a gas to one of the electrodes for causign a reduction in the reactive gas thereat and producing water, while applying another gas of known concentration to the other electrode to cause the oxidation thereof for producing an electronic charge that flows between the electrodes through an external circuit during the electrochemical reactions, whereby the sensor is operative up to of approximately 180 degrees Centigrade.

* * * * *

UNITED STATES PATENT AND TRADEMARK OFFICE
CERTIFICATE OF CORRECTION

PATENT NO. : 5,164,053

DATED : November 17, 1992

INVENTOR(S) : Mohammed Razaq et al

It is certified that error appears in the above-identified patent and that said Letters Patent is hereby corrected as shown below:

```
Column  2, line 17, after "membrane" insert --to--;
Column  2, line 18, after "room" delete "tempra" and substitute
              --tempera--;
Column  6, line 28, delete "plymeric" and substitute --polymeric--;
Column  6, line 31, after "may" delete "e" and substitute --be--;

Column  9, line 48, after "maintaining" delete "teh" and
              substitute --the--;
Column  9, line 57, delete "teh" and substitute --the--;
Column  9, line 68, delete "sensign" and substitute --sensing--;

Column 10, line 56, delete "lyaer" and substitute --layer--;
Column 10, line 69, delete "teh" and substitute --the--;

Column 11, line 10, delete "sensign" and substitute --sensing--;
Column 11, line 20, delete "ara" and substitute --area--.
```

Signed and Sealed this

Fifth Day of October, 1993

*Attest:*

BRUCE LEHMAN

*Attesting Officer*  Commissioner of Patents and Trademarks